(12) United States Patent
Shiba et al.

(10) Patent No.: US 7,462,462 B2
(45) Date of Patent: Dec. 9, 2008

(54) PEPTIDE CAPABLE OF BINDING TO NANOGRAPHITE STRUCTURES

(75) Inventors: Kiyotaka Shiba, Tokyo (JP); Daisuke Kase, Tokyo (JP); Sumio Iijima, Nagoya (JP)

(73) Assignees: Japanese Foundation For Cancer Research, Tokyo (JP); NEC Corporation, Tokyo (JP)

( * ) Notice: Subject to any disclaimer, the term of this patent is extended or adjusted under 35 U.S.C. 154(b) by 268 days.

(21) Appl. No.: 11/098,763

(22) Filed: Apr. 4, 2005

(65) Prior Publication Data

US 2005/0277160 A1 Dec. 15, 2005

Related U.S. Application Data

(63) Continuation-in-part of application No. PCT/JP2003/012766, filed on Oct. 6, 2003.

(30) Foreign Application Priority Data

Oct. 4, 2002 (JP) .............................. 2002-292951

(51) Int. Cl.
*G01N 33/53* (2006.01)
*A61K 38/00* (2006.01)
*A61K 38/04* (2006.01)
*C07K 5/00* (2006.01)
*C07K 7/00* (2006.01)
*C07K 16/00* (2006.01)
*C07K 17/00* (2006.01)

(52) U.S. Cl. ............................ 435/7.5; 514/13; 514/14; 530/325; 530/326

(58) Field of Classification Search ................ None
See application file for complete search history.

(56) References Cited

U.S. PATENT DOCUMENTS

| | | | | |
|---|---|---|---|---|
| 7,276,088 B2 * | 10/2007 | Huang et al. | .................. | 8/405 |
| 7,304,128 B2 * | 12/2007 | Jagota et al. | ................. | 530/327 |
| 2003/0113714 A1 * | 6/2003 | Belcher et al. | ................. | 435/5 |
| 2004/0202603 A1 * | 10/2004 | Fischer et al. | ............ | 423/447.2 |

FOREIGN PATENT DOCUMENTS

| | | |
|---|---|---|
| EP | 603672 | 6/1994 |
| JP | 2002-293794 | 10/2002 |
| WO | WO 03/026590 | 4/2003 |

OTHER PUBLICATIONS

H.J.C. Berendsen. A Glimpse of the Holy Grail? Science (1998) 282, pp. 642-643.*
Rudinger. In: Peptide Hormones, JA Parsons, Ed. (1976) 1-7.*
Sigma. Designing Custom Peptides. http://www.sigma-genosys.com/peptide_design.asp (Accessed Dec. 16, 2004), 2 pages.*
W.S. Messer, "Vasopressin and Oxytocin", web document updated Apr. 3, 2000; http://www.neurosci.pharm.utoledo.edu/MBC3320/vasopressin.htm; 5 pages.*
D.E. Smilek, et al. Proc. Natl. Acad. Sci. USA (1991) 88, pp. 9633-9637.*
D. Voet and J.G. Voet. Biochemistry, 2nd Edition.(1995), pp. 235-241☐☐.*
Iijima et al., Nano-aggregates of single-walled graphite carbon nanohorns, Chemical Physics Letters 309 (1999) 165-170.
Wang et al., Peptides with selective affinity for carbon nanotubes, Nature Materials, vol. 2, Mar. 2003, 196-200.
Whaley et al., Selection of peptides with semiconductor binding specificity for directed nanocrystal assembly, Nature, vol. 405, Jun. 2000, 665-668.
Zhu et al., Binary Nanomaterials Based on Nanocarbons: A Case for Probing Carbon Nanohorns' Biorecognition Properties, Nano Letters, 2003, vol. 3, 1033-1036.

* cited by examiner

*Primary Examiner*—Cecilia J Tsang
*Assistant Examiner*—Marcela M Cordero Garcia
(74) *Attorney, Agent, or Firm*—Frommer Lawrence & Haug LLP; Thomas J. Kowalski; Russell A. Garman

(57) ABSTRACT

It is intended to provide a peptide or a phage recognizing nanographite structures and thus enabling efficient recognition, binding, separation and alignment of nanographite structures such as carbon nanohorns or carbon nanotubes, an artificial protein or a chimeric molecule comprising the above-described peptide bonded to a functional peptide, a protein, a labeling, etc., and a complex of the above-described peptide molecule, artificial protein or chimeric molecule with a nanographite structure. By panning peptide-presenting phages bonded to nanographite structures, a nanographite structure-binding peptide capable of specifically recognizing nanographite structures such as carbon nanohorns or carbon nanotubes is obtained.

5 Claims, 9 Drawing Sheets

Fig. 3

| NHD12-5-1 | GHWHHITKVSKQ |
| NHD12-5-2 | DYFSSPYYEQLF |
| NHD12-5-12 | WPGWHHVPPAVS |
| NHD12-5-25 | SWHHKGVDYRP |
| NHD12-6-17 | WHPQQHWFDHSH |
| NHD12-6-23 | SSPYWSKPPVRW |

Fig. 4

| NHC-6-1 | YYPHPMF |
| NHC-6-2 | YDPFHII |
| NHC-6-11 | PTPWSRS |
| NHC-7-15 | NWWNHAR |
| NHC-7-16 | TWGHQFG |

Fig. 7

| BHiP5 | LLADTTHHRPWT |
| BHiP9 | TWWPYAHSTTPR |
| BHiP14 | GWWSRPMNHIYA |
| BHiP21 | YPSWYQRHYANP |
| BHiP31 | HYSWWRAPTPTP |
| BHiP34 | TWWGPHRVQMHT |
| BHiP35 | GPSPSPESPTRP |
| BHiP38 | SSPSLHRPVSWT |

Fig. 8

| BHiPC-9 | NPNSPSS |
| BHiPC-10 | NINNTSM |

| HiP1  | SHWWSWTTPLNG |
| HiP2  | SWWNWRLPSPPQ |
| HiP6  | SNWWPHPWSLRW |
| HiP9  | TWWGPWWSKTAI |
| HiP10 | FVPTFTVTHKPL |
| HiP16 | SHWWWWDARGYD |

Fig. 14

| Phage clones | Peptide sequences | N H | N T | Agglutination |
|---|---|---|---|---|
| NHD12-5-2 | DYFSSPYYEQLF | +++ | +++ | ○ |
| HiP2 | SWWNWRLPSPPQ | +++ | +++ | ○ |
| HiP6 | SNWWPHPWSLRW | +++ | +++ | ○ |
| BHiP14 | GWWSRPMNHIYA | ++ | +++ | ○ |
| BHiP21 | YPSWYQRHYANP | ++ | +++ | ○ |
| BHiP31 | HYSWWRAPTPTP | ++ | +++ | ○ |
| HiP9 | TWWGPWWSKTAI | ++ | +++ | ○ |
| HiP16 | SHWWWWDARGYD | ++ | +++ | ○ |
| NHD12-5-12 | WPGWHHVPPAVS | + | +++ | ○ |
| NHC-7-15 | NWWNHAR | + | +++ | ○ |
| BHiP9 | TWWPYAHSTTPR | + | +++ | ○ |
| BHiP34 | TWWGPHRVQMHT | + | +++ | ○ |
| HiP1 | SHWWSWTTPLNG | + | +++ | ○ |
| NHC-6-2 | YDPFHII | + | ++ | ○ |
| NHC-7-16 | TWGHQFG | + | ++ | ○ |
| NHD12-5-1 | GHWHHITKVSKQ | + | + | ○ |
| NHD12-5-25 | SWHHKHGVDYRP | + | + | ○ |
| NHD12-6-17 | WHPQQHWFDHSH | +/− | + | ○ |
| NHD12-6-23 | SSPYWSKPPVRW | +/− | + | ○ |
| NHC-6-1 | YYPHPMF | +/− | + | ○ |
| N2 | NSRLDLLPGVFH | +/− | +/− | × |
| N3 | QLHPKFSAGYSS | +/− | +/− | × |
| N4 | MPWYQLPPGPEN | +/− | +/− | × |
| NHC-6-11 | PTPWSRS | +/− | +/− | × |
| BHiP5 | LLADTTHHRPWT | +/− | +/− | × |
| BHiP35 | GPSPSPESPTRP | +/− | +/− | × |
| BHiP38 | SSPSLHRPVSWT | +/− | +/− | × |
| BHiPC-9 | NPNSPSS | +/− | +/− | × |
| BHiPC-10 | NINNTSM | +/− | +/− | × |
| HiP10 | FVPTFTVTHKPL | +/− | +/− | × |

```
                           SEQUENCE LISTING

<160> NUMBER OF SEQ ID NOS: 32

<210> SEQ ID NO 1
<211> LENGTH: 12
<212> TYPE: PRT
<213> ORGANISM: Artificial Sequence
<220> FEATURE:
<223> OTHER INFORMATION: Description of Artificial Sequence: Synthetic
      pNHD12-5-2 peptide

<400> SEQUENCE: 1

Asp Tyr Phe Ser Ser Pro Tyr Tyr Glu Gln Leu Phe
 1               5                  10

<210> SEQ ID NO 2
<211> LENGTH: 7
<212> TYPE: PRT
<213> ORGANISM: Artificial Sequence
<220> FEATURE:
<223> OTHER INFORMATION: Description of Artificial Sequence: Synthetic
      pNHC-6-2 peptide

<400> SEQUENCE: 2

Tyr Asp Pro Phe His Ile Ile
 1               5

<210> SEQ ID NO 3
<211> LENGTH: 12
<212> TYPE: PRT
<213> ORGANISM: Artificial Sequence
<220> FEATURE:
<223> OTHER INFORMATION: Description of Artificial Sequence: Synthetic
      pNHD12-5-1 peptide

<400> SEQUENCE: 3

Gly His Trp His His Ile Thr Lys Val Ser Lys Gln
 1               5                  10

<210> SEQ ID NO 4
<211> LENGTH: 12
<212> TYPE: PRT
<213> ORGANISM: Artificial Sequence
<220> FEATURE:
<223> OTHER INFORMATION: Description of Artificial Sequence: Synthetic
      pNHD12-5-12 peptide

<400> SEQUENCE: 4

Trp Pro Gly Trp His His Val Pro Pro Ala Val Ser
 1               5                  10

<210> SEQ ID NO 5
<211> LENGTH: 12
```

```
<212> TYPE: PRT
<213> ORGANISM: Artificial Sequence
<220> FEATURE:
<223> OTHER INFORMATION: Description of Artificial Sequence: Synthetic
      pNHD12-5-25 peptide

<400> SEQUENCE: 5

Ser Trp His His Lys His Gly Val Asp Tyr Arg Pro
 1               5                  10

<210> SEQ ID NO 6
<211> LENGTH: 12
<212> TYPE: PRT
<213> ORGANISM: Artificial Sequence
<220> FEATURE:
<223> OTHER INFORMATION: Description of Artificial Sequence: Synthetic
      pNHD12-6-17 peptide

<400> SEQUENCE: 6

Trp His Pro Gln Gln His Trp Phe Asp His Ser His
 1               5                  10

<210> SEQ ID NO 7
<211> LENGTH: 12
<212> TYPE: PRT
<213> ORGANISM: Artificial Sequence
<220> FEATURE:
<223> OTHER INFORMATION: Description of Artificial Sequence: Synthetic
      pNHD12-6-23 peptide

<400> SEQUENCE: 7

Ser Ser Pro Tyr Trp Ser Lys Pro Pro Val Arg Trp
 1               5                  10

<210> SEQ ID NO 8
<211> LENGTH: 7
<212> TYPE: PRT
<213> ORGANISM: Artificial Sequence
<220> FEATURE:
<223> OTHER INFORMATION: Description of Artificial Sequence: Synthetic
      pNHC-6-1 peptide

<400> SEQUENCE: 8

Tyr Tyr Pro His Pro Met Phe
 1               5

<210> SEQ ID NO 9
<211> LENGTH: 7
<212> TYPE: PRT
<213> ORGANISM: Artificial Sequence
<220> FEATURE:
<223> OTHER INFORMATION: Description of Artificial Sequence: Synthetic
      pNHC-7-15 peptide

<400> SEQUENCE: 9

Asn Trp Trp Asn His Ala Arg
 1               5

<210> SEQ ID NO 10
<211> LENGTH: 7
<212> TYPE: PRT
<213> ORGANISM: Artificial Sequence
<220> FEATURE:
<223> OTHER INFORMATION: Description of Artificial Sequence: Synthetic
      pNHC-7-16 peptide

<400> SEQUENCE: 10

Thr Trp Gly His Gln Phe Gly
```

-continued

```
<210> SEQ ID NO 11
<211> LENGTH: 12
<212> TYPE: PRT
<213> ORGANISM: Artificial Sequence
<220> FEATURE:
<223> OTHER INFORMATION: Description of Artificial Sequence: Synthetic
      pBHiP9 peptide

<400> SEQUENCE: 11

Thr Trp Trp Pro Tyr Ala His Ser Thr Thr Pro Arg
 1               5                  10

<210> SEQ ID NO 12
<211> LENGTH: 12
<212> TYPE: PRT
<213> ORGANISM: Artificial Sequence
<220> FEATURE:
<223> OTHER INFORMATION: Description of Artificial Sequence: Synthetic
      pBHiP14 peptide

<400> SEQUENCE: 12

Gly Trp Trp Ser Arg Pro Met Asn His Ile Tyr Ala
 1               5                  10

<210> SEQ ID NO 13
<211> LENGTH: 12
<212> TYPE: PRT
<213> ORGANISM: Artificial Sequence
<220> FEATURE:
<223> OTHER INFORMATION: Description of Artificial Sequence: Synthetic
      pBHiP21 peptide

<400> SEQUENCE: 13

Tyr Pro Ser Trp Tyr Gln Arg His Tyr Ala Asn Pro
 1               5                  10

<210> SEQ ID NO 14
<211> LENGTH: 12
<212> TYPE: PRT
<213> ORGANISM: Artificial Sequence
<220> FEATURE:
<223> OTHER INFORMATION: Description of Artificial Sequence: Synthetic
      pBHiP31 peptide

<400> SEQUENCE: 14

His Tyr Ser Trp Trp Arg Ala Pro Thr Pro Thr Pro
 1               5                  10

<210> SEQ ID NO 15
<211> LENGTH: 12
<212> TYPE: PRT
<213> ORGANISM: Artificial Sequence
<220> FEATURE:
<223> OTHER INFORMATION: Description of Artificial Sequence: Synthetic
      pBHiP34 peptide

<400> SEQUENCE: 15

Thr Trp Trp Gly Pro His Arg Val Gln Met His Thr
 1               5                  10

<210> SEQ ID NO 16
<211> LENGTH: 12
<212> TYPE: PRT
<213> ORGANISM: Artificial Sequence
<220> FEATURE:
<223> OTHER INFORMATION: Description of Artificial Sequence: Synthetic
```

```
       pHiP1 peptide

<400> SEQUENCE: 16

Ser His Trp Trp Ser Trp Thr Thr Pro Leu Asn Gly
1               5                   10

<210> SEQ ID NO 17
<211> LENGTH: 12
<212> TYPE: PRT
<213> ORGANISM: Artificial Sequence
<220> FEATURE:
<223> OTHER INFORMATION: Description of Artificial Sequence: Synthetic
      pHiP2 peptide

<400> SEQUENCE: 17

Ser Trp Trp Asn Trp Arg Leu Pro Ser Pro Pro Gln
1               5                   10

<210> SEQ ID NO 18
<211> LENGTH: 12
<212> TYPE: PRT
<213> ORGANISM: Artificial Sequence
<220> FEATURE:
<223> OTHER INFORMATION: Description of Artificial Sequence: Synthetic
      pHiP6 peptide

<400> SEQUENCE: 18

Ser Asn Trp Trp Pro His Pro Trp Ser Leu Arg Trp
1               5                   10

<210> SEQ ID NO 19
<211> LENGTH: 12
<212> TYPE: PRT
<213> ORGANISM: Artificial Sequence
<220> FEATURE:
<223> OTHER INFORMATION: Description of Artificial Sequence: Synthetic
      pHiP9 peptide

<400> SEQUENCE: 19

Thr Trp Trp Gly Pro Trp Trp Ser Lys Thr Ala Ile
1               5                   10

<210> SEQ ID NO 20
<211> LENGTH: 12
<212> TYPE: PRT
<213> ORGANISM: Artificial Sequence
<220> FEATURE:
<223> OTHER INFORMATION: Description of Artificial Sequence: Synthetic
      pHiP16 peptide

<400> SEQUENCE: 20

Ser His Trp Trp Trp Trp Asp Ala Arg Gly Tyr Asp
1               5                   10

<210> SEQ ID NO 21
<211> LENGTH: 12
<212> TYPE: PRT
<213> ORGANISM: Artificial Sequence
<220> FEATURE:
<223> OTHER INFORMATION: Description of Artificial Sequence: Synthetic
      CP02-58 peptide

<400> SEQUENCE: 21

Phe Gln Tyr Leu Tyr Ser Tyr Pro Phe Asp Ser Glu
1               5                   10

<210> SEQ ID NO 22
```

```
<211> LENGTH: 12
<212> TYPE: PRT
<213> ORGANISM: Artificial Sequence
<220> FEATURE:
<223> OTHER INFORMATION: Description of Artificial Sequence: Synthetic
      pN2 peptide

<400> SEQUENCE: 22

Asn Ser Arg Leu Asp Leu Leu Pro Gly Val Phe His
  1               5                  10

<210> SEQ ID NO 23
<211> LENGTH: 12
<212> TYPE: PRT
<213> ORGANISM: Artificial Sequence
<220> FEATURE:
<223> OTHER INFORMATION: Description of Artificial Sequence: Synthetic
      pN3 peptide

<400> SEQUENCE: 23

Gln Leu His Pro Lys Phe Ser Ala Gly Tyr Ser Ser
  1               5                  10

<210> SEQ ID NO 24
<211> LENGTH: 12
<212> TYPE: PRT
<213> ORGANISM: Artificial Sequence
<220> FEATURE:
<223> OTHER INFORMATION: Description of Artificial Sequence: Synthetic
      pN4 peptide

<400> SEQUENCE: 24

Met Pro Trp Tyr Gln Leu Pro Pro Gly Pro Glu Asn
  1               5                  10

<210> SEQ ID NO 25
<211> LENGTH: 7
<212> TYPE: PRT
<213> ORGANISM: Artificial Sequence
<220> FEATURE:
<223> OTHER INFORMATION: Description of Artificial Sequence: Synthetic
      pNHC-6-11 peptide

<400> SEQUENCE: 25

Pro Thr Pro Trp Ser Arg Ser
  1               5

<210> SEQ ID NO 26
<211> LENGTH: 12
<212> TYPE: PRT
<213> ORGANISM: Artificial Sequence
<220> FEATURE:
<223> OTHER INFORMATION: Description of Artificial Sequence: Synthetic
      pBHiP5 peptide

<400> SEQUENCE: 26

Leu Leu Ala Asp Thr Thr His His Arg Pro Trp Thr
  1               5                  10

<210> SEQ ID NO 27
<211> LENGTH: 12
<212> TYPE: PRT
<213> ORGANISM: Artificial Sequence
<220> FEATURE:
<223> OTHER INFORMATION: Description of Artificial Sequence: Synthetic
      pBHiP35 peptide

<400> SEQUENCE: 27
```

Gly Pro Ser Pro Ser Pro Glu Ser Pro Thr Arg Pro
1               5                   10

<210> SEQ ID NO 28
<211> LENGTH: 12
<212> TYPE: PRT
<213> ORGANISM: Artificial Sequence
<220> FEATURE:
<223> OTHER INFORMATION: Description of Artificial Sequence: Synthetic
      pBHiP38 peptide

<400> SEQUENCE: 28

Ser Ser Pro Ser Leu His Arg Pro Val Ser Trp Thr
1               5                   10

<210> SEQ ID NO 29
<211> LENGTH: 7
<212> TYPE: PRT
<213> ORGANISM: Artificial Sequence
<220> FEATURE:
<223> OTHER INFORMATION: Description of Artificial Sequence: Synthetic
      pBHiPC-9 peptide

<400> SEQUENCE: 29

Asn Pro Asn Ser Pro Ser Ser
1               5

<210> SEQ ID NO 30
<211> LENGTH: 7
<212> TYPE: PRT
<213> ORGANISM: Artificial Sequence
<220> FEATURE:
<223> OTHER INFORMATION: Description of Artificial Sequence: Synthetic
      pBHiPC-10 peptide

<400> SEQUENCE: 30

Asn Ile Asn Asn Thr Ser Met
1               5

<210> SEQ ID NO 31
<211> LENGTH: 12
<212> TYPE: PRT
<213> ORGANISM: Artificial Sequence
<220> FEATURE:
<223> OTHER INFORMATION: Description of Artificial Sequence: Synthetic
      pHiP10 peptide

<400> SEQUENCE: 31

Phe Val Pro Thr Phe Thr Val Thr His Lys Pro Leu
1               5                   10

<210> SEQ ID NO 32
<211> LENGTH: 20
<212> TYPE: DNA
<213> ORGANISM: Artificial Sequence
<220> FEATURE:
<223> OTHER INFORMATION: Description of Artificial Sequence: Synthetic
      -96gIII primer

<400> SEQUENCE: 32
ccctcatagt tagcgtaacg                                                    20

PEPTIDE CAPABLE OF BINDING TO NANOGRAPHITE STRUCTURES

This application is a continuation-in-part application of international patent application Serial No. PCT/JP2003/012766 filed Oct. 6, 2003, which published as PCT Publication No. WO2004/031381 on Apr. 15, 2004, which claims benefit of Japanese patent application Serial No. JP 2002-292951 filed Oct. 4, 2002.

The foregoing applications, and all documents cited therein or during their prosecution ("appln cited documents") and all documents cited or referenced in the appln cited documents, and all documents cited or referenced herein ("herein cited documents"), and all documents cited or referenced in herein cited documents, together with any manufacturer's instructions, descriptions, product specifications, and product sheets for any products mentioned herein or in any document incorporated by reference herein, are hereby incorporated herein by reference, and may be employed in the practice of the invention. Citation or identification of any document in this application is not an admission that such document is available as prior art to the present invention. It is noted that in this disclosure and particularly in the claims and/or paragraphs, terms such as "comprises", "comprised", "comprising" and the like can have the meaning attributed to it in U.S. Patent law; e.g., they can mean "includes", "included", "including", and the like; and that terms such as "consisting essentially of" and "consists essentially of" have the meaning ascribed to them in U.S. Patent law, e.g., they allow for elements not explicitly recited, but exclude elements that are found in the prior art or that affect a basic or novel characteristic of the invention. The embodiments of the present invention are disclosed herein or are obvious from and encompassed by, the detailed description. The detailed description, given by way of example, but not intended to limit the invention solely to the specific embodiments described, may best be understood in conjunction with the accompanying drawings.

TECHNICAL FIELD

The present invention relates to: a peptide molecule or a phage recognizing nanographite structures such as carbon nanohorns and carbon nanotubes, which are carbon materials; an artificial protein or a chimeric molecule comprising the peptide molecule bound to a functional peptide or protein, or a labeled material, etc.; a complex formed from the peptide molecule, the artificial protein or the chimeric molecule, and a nanographite structure. For example, a complex, formed from a compound of graphite structure having a nanometer-scale fine structure and a peptide, an artificial protein or a chimeric molecule which recognizes the compound specifically, can be advantageously used for nanobiotechnology, material engineering, semiconductors, pharmaceuticals, cosmetics, etc.

BACKGROUND ART

As a crystal structure of carbon, diamond and graphite have been known from long time ago, and (C60) was found by R. E. Smalley, R. F. Curl and H. W. Kroto et al., in 1985 (Nature, 318: 162-163, 1985). C60 has a soccer ball-like structure comprising 12 pentagons and 20 hexagons, and other than C60, there are large basket-like molecules such as C70 and C76, and this series of molecules is called "fullerene". Further, carbon compounds with new structures previously unknown, such as "carbon nanotube" (Nature, 354: 56-58, 1991; Japanese Laid-Open Patent Application No. 2001-64004) and "carbon nanohorn" (Chem. Phys. Lett., 309, 165-170, 1999; Japanese Laid-Open Patent Application No. 2001-64004) were successively discovered by one of the present inventors, Sumio Iijima, in 1991 and 1999, respectively. All of these fullerenes, carbon nanotubes and carbon nanohorns comprise six- and five-membered rings of carbon atoms, and form nanometer-scale fine structures, and therefore, they have got a lot of attention as "nanographite structure" recently.

The reasons why nanographite structures get a lot of attention include: "carbon nanotubes can have both properties of metal and semiconductor due to the difference in their chirality (Nature, 391: 59-62, 1998)", "metal-doped fullerene exhibits superconductivity (Nature, 350: 600-601, 1991)", "selective gas storage capability shown by carbon nanohorns (Nikkei Science, August issue, 42, 2002)". With the use of these characteristic properties, nanographite structures are expected to be applied to new electrical materials, catalysts, optical materials, and other such fields, more specifically, to wiring of semiconductors, fluorescent indicator tubes, fuel cells, gas storage, carriers for gene therapy, cosmetics, drug delivery systems, biosensors, etc.

As mentioned above, when application of nanographite structures is considered in various fields, techniques for efficient recognition, binding, separation, alignment of carbon nanotubes, carbon nanohorns or modified materials thereof, are required. However, there is a problem that it is hard to use nanographite structures such as carbon nanohorns and carbon nanotubes because, in general, there is no method for recognizing, binding them specifically. The object of the present invention is to provide: a peptide or a phage recognizing nanographite structures which allows efficient recognition, binding, separation, alignment of nanographite structures such as carbon nanohorns and carbon nanotubes; an artificial protein or a chimeric molecule comprising the peptide bound to a functional peptide or protein, or a labeled material, etc.; a complex formed from the peptide molecule, the artificial protein or the chimeric molecule, and a nanographite structure.

The present inventors have conducted keen study to attain the above-mentioned object, and have found that peptides capable of binding to nanographite structures, which specifically recognize nanographite structures such as carbon nanohorns and carbon nanotubes, etc., can be obtained by a process comprising steps of: treating a nanographite structure with nitric acid to construct a carboxyl group on the nanographite structure; biotinylating the carboxyl group; solid-phasing the biotinylated nanographite structure on a magnetic bead coated with streptavidin; repeating a panning operation to concentrate a phage clone binding to a nanographite structure, wherein said panning operation comprises following steps: a phage population wherein various peptide sequences are displayed on phage particles is brought into contact with the solid-phased nanographite structure; the solid-phased nanographite structure to which phage particles have bound through the peptide sequences is collected with a permanent magnet; phage particles bound to the obtained nanographite structure are proliferated in *E. coli;* then a proliferated phage population wherein peptide sequences are displayed on phage particles is brought into contact with the solid-phased nanographite structure again. Thus the present invention has been completed.

DISCLOSURE OF THE INVENTION

The present invention relates to a method for screening a peptide capable of binding to a nanographite structure comprising steps of: treating a nanographite structure with nitric acid to construct a carboxyl group on the nanographite structure; biotinylating the carboxyl group; solid-phasing the biotinylated nanographite structure on a magnetic bead coated with streptavidin; repeating a panning operation to concentrate a phage clone binding to the nanographite structure, wherein said panning operation comprises following steps: a phage population wherein different peptide sequences are displayed on phage particles is brought into contact with the solid-phased nanographite structure; the solid-phased nanographite structure to which phage particles have bound through the peptide sequences is collected with a permanent magnet; phage particles bound to the obtained nanographite structure are proliferated in bacterial cells; then a proliferated phage population wherein the peptide sequences are displayed on phage particles is brought into contact with the solid-phased nanographite structure ("1"), a peptide capable of binding to a nanographite structure, which is obtained by the method for screening according to "1" ("2").

The present invention also relates to a peptide capable of binding to a nanographite structure, which comprises an amino acid sequence shown by any one of Seq. ID Nos. 1 to 20 ("3"), a peptide capable of binding to a nanographite structure, which can bind to a nanographite structure containing whole or part of an amino acid sequence shown by any one of Seq. ID Nos. 1 to 20 ("4"), the peptide capable of binding to a nanographite structure according to any one of "2" to "4", wherein the amino acid sequence is DYFSSPYYEQLF (Seq. ID No. 1) ("5"), the peptide capable of binding to a nanographite structure according to any one of "2" to "4", wherein the amino acid sequence is YDPFHII (Seq. ID No. 2) ("6"), the peptide capable of binding to a nanographite structure according to any one of "2" to "6", which is chemically modified ("7"), the peptide capable of binding to a nanographite structure according to any one of "2" to "7", wherein the nanographite structure is a carbon nanohorn or a carbon nanotube ("8"), the peptide capable of binding to a nanographite structure according to "8", wherein the carbon nanohorn or the carbon nanotube has a single-wall structure of thickness corresponding to the size of a carbon atom ("9"), the peptide capable of binding to a nanographite structure according to "8" or "9", wherein the carbon nanohorn or the carbon nanotube is constituted of a carbon structure to which a functional group is added ("10").

The present invention further relates to a phage capable of binding to a nanographite structure, which displays a peptide comprising an amino acid sequence shown by any one of Seq. ID Nos. 1 to 20 on its particle surface ("11"), a phage capable of binding to a nanographite structure, which displays a peptide capable of binding to a nanographite structure containing whole or part of an amino acid sequence shown by any one of Seq. ID Nos. 1 to 20 on its particle surface ("12"), the phage capable of binding to a nanographite structure according to "11" or "12", wherein the amino acid sequence shown by any one of Seq. ID Nos. 1 to 20 is DYFSSPYYEQLF (Seq. ID No. 1) ("13"), the phage capable of binding to a nanographite structure according to "11" or "12", wherein the amino acid sequence shown by any one of Seq. ID Nos. 1 to 20 is YDPFHII (Seq. ID No. 2) ("14"), the phage capable of binding to a nanographite structure according to any one of "11" to "14", wherein the nanographite structure is a carbon nanohorn or a carbon nanotube ("15"), the phage capable of binding to a nanographite structure according to "15", wherein the carbon nanohorn or the carbon nanotube has a single-wall structure of thickness corresponding to the size of a carbon atom ("16"), the phage capable of binding to a nanographite structure according to "15" or "16", wherein the carbon nanohorn or the carbon nanotube is constituted of a carbon structure to which a functional group is added ("17").

The present invention further relates to an artificial protein capable of binding to a nanographite structure comprising a peptide comprising an amino acid sequence shown by any one of Seq. ID Nos. 1 to 20, or a peptide capable of binding to a nanographite structure containing whole or part of the amino acid sequence, bound to a functional peptide or protein ("18"), the artificial protein capable of binding to a nanographite structure according to "18", wherein the functional peptide or protein can form a two-dimensional crystal through self-assembly in cooperation with a peptide capable of binding to a nanographite structure ("19"), the artificial protein capable of binding to a nanographite structure according to "18", wherein the functional peptide or protein has a peptide sequence with cell-recognizing activity ("20"), the artificial protein capable of binding to a nanographite structure according to any one of "18" to "20", wherein the amino acid sequence is DYFSSPYYEQLF (Seq. ID No. 1) ("21"), the artificial protein capable of binding to a nanographite structure according to any one of "18" to "20", wherein the amino acid sequence is YDPFHII (Seq. ID No. 2) ("22"), the artificial protein capable of binding to a nanographite structure according to any one of "18" to "22", wherein the peptide capable of binding to a nanographite structure is chemically modified ("23"), the artificial protein capable of binding to a nanographite structure according to any one of "18" to "23", wherein the nanographite structure is a carbon nanohorn or a carbon nanotube ("24"), the artificial protein capable of binding to a nanographite structure according to "24", wherein the carbon nanohorn or the carbon nanotube has a single-wall structure of thickness corresponding to the size of a carbon atom ("25"), the artificial protein capable of binding to a nanographite structure according to "24" or "25", wherein the carbon nanohorn or the carbon nanotube is constituted of a carbon structure to which a functional group is added ("26").

The present invention further relates to a chimeric molecule capable of binding to a nanographite structure comprising a peptide comprising an amino acid sequence shown by any one of Seq. ID Nos. 1 to 20, or a peptide capable of binding to a nanographite structure containing whole or part of the amino acid sequence, bound to a labeled material or a peptide tag that can generate a detectable signal alone or by reacting with other material ("27"), a chimeric molecule capable of binding to a nanographite structure comprising a peptide comprising an amino acid sequence shown by any one of Seq. ID Nos. 1 to 20, or a peptide capable of binding to a nanographite structure containing whole or part of the amino acid sequence, bound to a nonpeptide compound ("28"), the chimeric molecule capable of binding to a nanographite structure according to "27" or "28", wherein the amino acid sequence is DYFSSPYYEQLF (Seq. ID No. 1) ("29"), the chimeric molecule capable of binding to a nanographite structure according to "27" or "28", wherein the amino acid sequence is YDPFHII (Seq. ID No. 2) ("30"), the chimeric molecule capable of binding to a nanographite structure according to any one of "27" to "30", wherein the peptide capable of binding to a nanographite structure is chemically modified ("31"), the chimeric molecule capable of binding to a nanographite structure according to any one of "27" to "31", wherein the nanographite structure is a carbon nanohorn or a carbon nanotube ("32"), the chimeric molecule capable of binding to a nanographite structure according to "32", wherein the carbon nanohorn or the carbon nanotube has a single-wall structure of thickness corresponding to the size of a carbon atom ("33"), the chimeric molecule capable of binding to a nanographite structure according to "32" or "33", wherein the carbon nanohorn or the carbon nanotube is constituted of a carbon structure to which a functional group is added ("34").

The present invention further relates to a nanographite structure complex wherein a peptide comprising an amino acid sequence shown by any one of Seq. ID Nos. 1 to 20, or a peptide capable of binding to a nanographite structure containing whole or part of the amino acid sequence, the artificial protein capable of binding to a nanographite structure according to any one of "18" to "26", or the chimeric molecule capable of binding to a nanographite structure according to any one of "27" to "34" is bound to a nanographite structure ("35"), the nanographite structure complex according to "35", wherein the amino acid sequence is DYFSSPYYEQLF (Seq. ID No. 1) ("36"), the nanographite structure complex according to "35", wherein the amino acid sequence is YDPF-HII (Seq. ID No. 2) ("37"), the nanographite structure complex according to any one of "35" to "37", wherein the peptide capable of binding to a nanographite structure is chemically modified ("38"), the nanographite structure complex according to any one of "35" to "38", wherein the nanographite structure is a carbon nanohorn or a carbon nanotube ("39"), the nanographite structure complex according to "39", wherein the carbon nanohorn or the carbon nanotube has a single-wall structure of thickness corresponding to the size of a carbon atom ("40"), the nanographite structure complex according to "39" or "40", wherein the carbon nanohorn or the carbon nanotube is constituted of a carbon structure to which a functional group is added ("41").

The present invention further relates to a synthetic peptide capable of binding to a nanographite structure, which comprises an amino acid sequence abundant in tryptophan (W), phenylalanine (F), tyrosine (Y), histidine (H), obtained by extracting sequence characteristics of amino acid sequences shown by Seq. ID Nos. 1 to 20 ("42"), the synthetic peptide capable of binding to a nanographite structure according to "42", wherein the nanographite structure is a carbon nanohorn or a carbon nanotube ("43"), the synthetic peptide capable of binding to a nanographite structure according to "43", wherein the carbon nanohorn or the carbon nanotube has a single-wall structure of thickness corresponding to the size of a carbon atom ("44"), the synthetic peptide capable of binding to a nanographite structure according to "43" or "44", wherein the carbon nanohorn or the carbon nanotube is constituted of a carbon structure to which a functional group is added ("45"), a DNA which encodes a peptide comprising an amino acid sequence shown by Seq. ID Nos. 1 to 20, or a peptide capable of binding to a nanographite structure containing whole or part of the amino acid sequence ("46").

BRIEF DESCRIPTION OF DRAWINGS

FIG. 3 is a chart showing clone names of phage clones obtained by the panning experiment of D12 peptide display library to the solid-phased carbon nanohorns in Example 1 of the present invention, and peptide sequences displayed by the phages. Figure discloses SEQ ID NOS: 3, 1 and 4-7. respectively, in order of appearance.

FIG. 4 is a chart showing clone names of phage clones obtained by the panning experiment of C7C peptide display library to the solid-phased carbon nanohorns in Example 1 of the present invention, and peptide sequences displayed by the phages. Figure discloses SEQ ID NOS: 8, 2, 25, 9 and 10, respectively, in order of appearance.

FIG. 7 is a chart showing clone names of phage clones obtained by the panning experiment of D12 peptide display library to the solid-phased carbon nanotubes in Example 2 of the present invention, and peptide sequences displayed by the phages. Figure discloses SEQ ID NOS: 26, 11, 12-15, 27 and 28, respectively, in order of appearance.

FIG. 8 is a chart showing clone names of phage clones obtained by the panning experiment of C7C peptide display library to the solid-phased carbon nanotubes in Example 2 of the present invention, and peptide sequences displayed by the phages. Figure discloses SEQ ID NOS: 29 and 30, respectively, in order of appearance.

FIG. 14 is a chart showing a summary of the binding ability of each phage clone to the solid-phased carbon nanohorns and the solid-phased single-wall carbon nanotubes and the result of the agglutination test of oxygen-treated carbon nanohorns obtained in Example 4 of the present invention, together with the tendency of peptide sequences. The number of "+" indicates the strength of binding ability obtained by the experiment in FIG. 11, and the number is proportional to the strength. "+/−" means that significant difference in comparison to control was not observed. NH and NT show the result of binding to carbon nanohorns and carbon nanotubes, respectively. "o" and "x" indicate the results of the experiment in FIG. 12, wherein agglutination of oxygen-treated carbon nanohorns was observed and not observed, respectively. Tryptophan (W), phenylalanine (F), and tyrosine (Y) are underlined. Histidine (H) is indicated by bold face. Figure discloses SEQ ID NOS: 1, 17, 18, 12-14, 19, 20, 4, 9, 11, 15, 16, 2, 10, 3, 5-8 and 22-31, respectively, in order of appearance.

BEST MODE OF CARRYING OUT THE INVENTION

Figure 1:
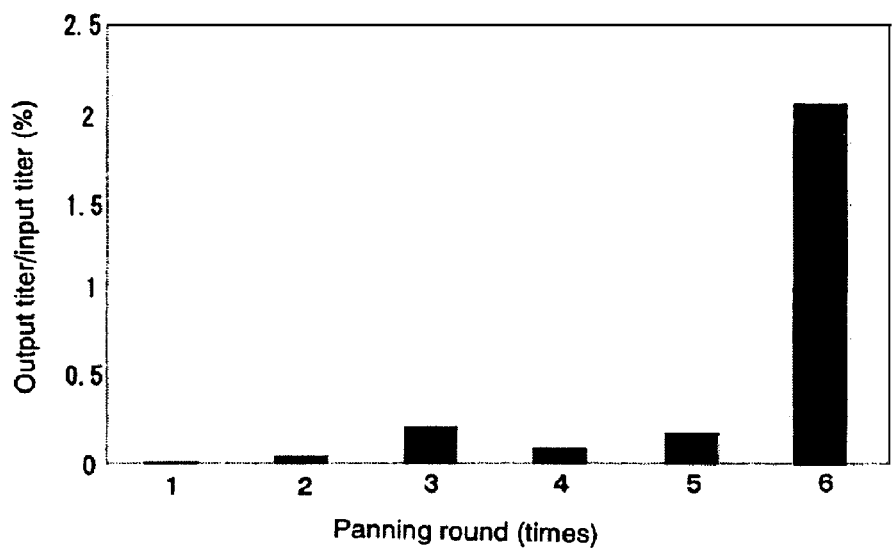
FIG. 1 is a graph showing the result of the panning experiment of D12 peptide display library to the solid-phased carbon nanohorns in Example 1 of the present invention. The ratio of output titer to input titer of each panning round is shown.

As the peptide capable of binding to nanographite structures of the present invention, a peptide which comprises an amino acid sequence shown by any one of Seq. ID Nos. 1 to 20, and a peptide which can bind to nanographite structures containing whole or part of an amino acid sequence shown by any one of Seq. ID Nos. 1 to 20 (hereinafter, these peptides are referred to as "the present peptide") are exemplified. The peptide capable of binding to nanographite structures of the present invention can be obtained by the method for screening a peptide capable of binding to nanographite structures comprising steps of: treating a nanographite structure with nitric acid to construct a carboxyl group on the nanographite structure; biotinylating the carboxyl group; solid-phasing the biotinylated nanographite structure on a magnetic bead coated with streptavidin; repeating a panning operation to concentrate a phage clone binding to the nanographite structure, wherein said panning operation comprises following steps: a phage population wherein different peptide sequences are displayed on phage particles is brought into contact with the solid-phased nanographite structure; the solid-phased nanographite structure to which phage particles have bound through the peptide sequences is collected with a permanent magnet; phage particles bound to the obtained nanographite structure are proliferated in bacterial cells; then a proliferated phage population wherein the peptide sequences are displayed on phage particles is brought into contact with the solid-phased nanographite structure. Further, the present invention includes a peptide capable of binding to nanographite structures which comprises an amino acid sequence other than an amino acid sequence shown by any one of Seq. ID Nos. 1 to 20, which can be obtained by this method for screening. The peptide capable of binding to nanographite structures of the present invention can be constructed also by synthesis based on its amino acid sequence information, and purified ones are preferable. The peptides displayed on phage particles are excluded from the above-mentioned peptide of the present invention. In addition, DNA that encodes the peptide capable of binding to nanographite structures of the present invention is not particularly limited as long as it encodes the present peptide.

As the phage capable of binding to nanographite structures of the present invention, any phage can be used as long as it displays the present peptide on its particle surface, and the phage capable of binding to nanographite structures can be obtained, as a phage clone binding to nanographite structures, by separating a peptide-displaying phage strongly bound to a molecule of a graphite structure from other phage population in the process of the aforementioned screening, or can be obtained by incorporating DNA which encodes the present peptide into a phagemid vector in the usual manner to transform a host cell such as *E. coli*, and infecting it with a helper phage. Generally, in high concentrations, filamentous phages such as M13 and fd go into a liquid crystalline state and have an orderly aligned structure. Therefore, by making a peptide phage recognizing a nanographite structure in a liquid crystalline state, a peptide recognizing a nanographite structure can be orderly aligned on a nanoscale. When a nanographite structure is brought into contact with a peptide in such state, the nanographite structure can be orderly aligned by the ability of the peptide to recognize nanographite structures.

The artificial protein capable of binding to nanographite structures of the present invention is not particularly limited as long as it comprises the present peptide bound to a functional peptide or protein. Examples of functions of the functional peptide or protein include: function to form secondary structures such as α-helix easily, antigenic function to induce neutralizing antibodies of viruses, etc., immunostimulation function (Nature Medicine, 3: 1266-1270, 1997), function to promote or inhibit cell proliferation, function to recognize cancer cells specifically, protein transduction function, apoptosis-inducing function, antigen determinant-presenting function, metal-binding function, coenzyme-binding function, catalyst activation function, fluorescent coloring activation function, function to bind to a specific receptor and activate the receptor, function to bind to a specific factor involved in signaling and to modulate its action, function to recognize a biopolymer such as protein, DNA, RNA, saccharide, specifically, cell adhesion function, function to localize a protein extracellularly, function to target a specific subcellular organelle (mitochondorion, chloroplast, ER, etc.), function to be embedded in cell membranes, function to form amyloid fibers, function to form fibrous proteins, function to form proteinous gels, function to form proteinous films, function to form monomolecular films, self-assembly function wherein two-dimensional crystals can be formed by self-assembly, etc., function to form particles, function to support formation of higher-order structures of other proteins. These artificial proteins can be constructed by combining functional peptides or proteins with peptides capable of binding to nanographite structures at amino acid level or DNA level, directly or indirectly.

Among the functional peptides or proteins mentioned above, for example, when a peptide or a protein which can form a two-dimensional crystal through self-assembly in cooperation with a peptide capable of binding to nanographite structures is used, an artificial protein, wherein a nanographite compound can be orderly aligned on a nanoscale along with the two-dimensional crystal, can be constructed. Examples of the peptide or the protein which can form a two-dimensional crystal through self-assembly in cooperation with a peptide capable of binding to nanographite structures include viruses (for instance, adenoviruses, rotaviruses, polioviruses, HK97, CCMV, etc.), ferritin family such as ferritin and apoferritin, DpsA proteins and MrgA proteins. Other example of the peptide or the protein which can form a two-dimensional crystal through self-assembly includes an artificially designed artificial protein having a lot of repetitions. Further, an example of a method for constructing a two-dimensional crystal of protein includes a method wherein a protein solution is developed on a water surface as a monomolecular film, and is adsorbed onto a solid substrate.

Among the functional peptides or proteins mentioned above, for example, when a peptide or a protein having a peptide sequence with cell recognition activity such as cell adhesion activity is used, an artificial protein with combined activity which recognizes nanographite compounds and cells simultaneously can be obtained. As the peptide or the protein having a peptide sequence with cell recognition activity such as cell adhesion activity, various ligands, monoclonal antibodies and their variable regions, single-stranded antibodies, etc., are exemplified. In addition to the natural proteins mentioned above, artificial proteins containing a peptide with cell adhesion activity are exemplified.

As a chimeric molecule capable of binding to nanographite structures of the present invention, a chimeric molecule comprising the present peptide bound to a labeled material or a peptide tag that can generate a detectable signal alone or by reacting with other material is exemplified. Examples of the labeled material include enzymes, fluorescent materials, chemiluminescent materials, radioisotopes, and Fc region of antibodies. Specifically, enzymes such as peroxydase (for instance, horseradish peroxydase), alkaline phosphatase, β-D-galactosidase, glucose oxydase, glucose-6-phosphate dehydrogenase, alcohol dehydrogenase, malic dehydrogenase, penicillinase, catalase, apoglucose oxydase, urease, luciferase or acetylcholine esterase; fluorescent materials such as fluorescein isothiocyanate, phycobiliprotein, rare-earth metal chelate, dansyl chloride or tetramethyl rhodamine isothiocyanate; radioisotopes such as $^3H$, $^{14}C$, $^{125}I$; chemiluminescent materials, are exemplified. In addition, examples of the peptide tag include conventionally known ones, specifically, epitope tags such as HA, FLAG, Myc; affinity tags such as GST, maltose-binding protein, biotinylated peptide, oligohistidine (His). For example, a nanographite structure complex can be easily purified with the use of affinity of His tag and Ni-NTA.

As a chimeric molecule capable of binding to nanographite structures of the present invention, a chimeric molecule comprising the present peptide bound to a nonpeptide compound is exemplified. Among the nonpeptide compounds, specific examples of nonpeptide low-molecule compounds include fluorescent dyes such as fluorescein and rhodamine, and antibiotics such as chloramphenicol and ampicillin. Specific examples of nonpeptide macro-molecule compounds include polystyrene, polypropylene, polyethylene, glass beads, silica gel, polysaccharides (including derivatives), polyalkyleneglycol such as polyethyleneglycol.

As a nanographite structure complex of the present invention, a complex comprising the present peptide, the artificial protein capable of binding to nanographite structures of the present invention, or the chimeric molecule capable of binding to nanographite structures of the present invention bound to a nanographite structure by any one of weak bindings such as hydrophobic bond, pai electron bond, van der Waals binding, ionic bond, or combination thereof, is exemplified.

Further, among the amino acid sequence shown by any one of Seq. ID Nos. 1 to 20 in the present peptide, a peptide comprising the amino acid sequence DYFSSPYYEQLF (Seq. ID No. 1) or the amino acid sequence YDPFHII (Seq. ID No. 2) is preferable in that it has excellent ability to bind to nanographite structures. As the present peptide and the peptide capable of binding to nanographite structures thus described, chemically modified peptides can be advantageously used. As the chemical modification, chemical modification comprising substitution with amino acid having a functional group, and chemical modification for easier binding to linkers are exemplified, and chemical modification which does not decrease the ability to bind to nanographite structures is preferable. Specific example of the chemical modification for easier binding to linkers includes a covalent bond of biotin to an amino group of a peptide by using N-hydroxysuccinimide ester of biotin. The aforementioned chimeric molecule is easily constructed by the biotinylation of peptide.

As the nanographite structure, nanometer-scale fine structures comprising six- and five-membered rings of carbon atoms such as carbon nanotubes, carbon nanohorns, carbon nanocapsuls, fullerenes, etc., are exemplified. Preferable examples of the carbon nanohorn or the carbon nanotube include those which have a single-wall structure of thickness corresponding to the size of a carbon atom, those which show hydrophilicity and are constituted of a carbon structure to which a functional group such as a carbonyl group, a carboxyl group, a hydroxyl group, an ether group, an imino group, a nitro group, a sulfone group, is added (Japanese Patent Application No. 2001-294499). For instance, a hydrophilic carbon nanohorn having a single-wall structure of thickness corresponding to the size of a carbon atom is constructed by conducting an oxidization treatment with an acid having oxidizing ability such as nitric acid, sulfic acid, hydracid peroxide in order to change the property of a carbon nanohorn, which is originally hydrophobic, to hydrophilic.

The present invention is now described more specifically with reference to Examples, however, the technical scope of the present invention is not limited thereto.

EXAMPLE 1

The surface of carbon in a form of a sinterd round bar in ambient gas pressure of $6 \times 10^4$ Pa of Ar gas was ablated with high-power $CO_2$ gas laser beam (output power 100 W, pulse width 20 ms, continuous wave), and the resultant soot-like substance was suspended in ethanol, then ultrasonic agitation (frequency 40 kHz, 60 minutes) and decantation were repeated 4 times to obtain single-wall carbon nanohorns. About 200 mg of the single-wall carbon nanohorns was put into 40 ml of nitric acid at a concentration of about 70%, and reflux was conducted for 1 hour at 130° C. After the reflux, the resultant was neutralized and washed by repeating dilution with ion-exchange water, centrifugation, and disposal of the supernatant, and water-soluble single-wall carbon nanohorns having a functional group (including a carboxyl group) were prepared.

1.2 mg of nitric acid-treated carbon nanohorns was suspended in 2 ml of 0.1 M 2-morpholinoethanesulfonic acid monohydrate (hereinafter referred to as MES, Dojindo, Kumamoto) (pH 5.5). This suspension was poured into a spitz tube for ultrasonic apparatuses (AS-1000, Tosho Electronics Ltd.), and completely suspended by ultrasonic agitation at output power 200 W for 1 hour using an ultrasonic cell disrupter (Biorupter, Cosmo Bio Co., Ltd., Tokyo). Then, the suspension was poured into 1.8 ml plastic tubes by 500 µl each, and 25 µl of 50 mM 5-(biotinamido)pentylamine (EZ-Link, Pierce Biotechnology, Inc., Rockford) was added into each tube, and the resultant solution was agitated. Immediately after that, 6.25 µl of 100 mg/ml 1-ethyl-3-[3-dimethylaminopropyl]carbodiimide hydrochloride (hereinafter referred to as EDC, Pierce Biotechnology, Inc.) solution prepared with 0.1 M MES (pH 5.5) was added into each tube, and the resultant solution was incubated for 2 hours while being agitated well at room temperature with the use of a microincubator (M-36, Taitec, Tokyo). As a result, amide bond was formed by the action of carbodiimide between a carboxyl group of a nitric acid-treated carbon nanohom and an amino group of biotin, consequently a biotinylated carbon nanohom was obtained.

10 mg/ml streptavidin-coated magnetic bead suspension (Dynabeads M-280, Dynal Biotech, Oslo) was washed twice with 0.1% polyoxyethylenesorbitan monolaurate [hereinafter referred to as Tween-20 (Sigma, St. Louis)], 50 mM Tris-buffered saline [hereinafter referred to as TBS, (pH 7.5)], and prepared so that beads were adjusted to 5 mg/ml in 0.1% Tween-20, 50 mM TBS, finally. Washing of streptavidin-coated magnetic beads was conducted with a magnetic particle concentrator (MPC-E, Dynal Biotech, Oslo) by adsorbing magnetic beads with a magnet from outside the tube.

120 μl of 0.1 M MES suspension of biotinylated carbon nanohorns (0.6 mg/ml, corresponding to about 70 μg of carbon nanohorns), 100 μl of 5 mg/ml pretreated streptavidin-coated magnetic bead suspension (0.1% Tween-20, 50 mM TBS) were mixed and agitated by patting the tube with fingers every 30 minutes, and an adsorption reaction was conducted for 4 hours at room temperature. Then, the mixture was washed twice with 200 μl of 2% bovine serum albumin (Iwai Chemicals Company Ltd., Tokyo), 50 mM TBS, and re-suspended in 200 μl of the same buffer and the suspension was incubated for 20 minutes at room temperature. Further, 10 μl of 1 mM d-biotin (Sigma), 2% bovine serum albumin, 50 mM TBS were added and the resultant mixture was incubated for 5 minutes at room temperature. By this operation, biotin-binding sites of streptavidin were saturated with biotin.

As phage display peptide libraries, D12 library which displays a linear random peptide comprising 12 residues (NEB, Beverly) and C7C library which displays a cyclized random peptide comprising 7 residues (NEB) were used. These are libraries having $2.7 \times 10^9$ and $1.2 \times 10^9$ different peptide sequences, respectively.

100 μl of suspension of magnetic beads wherein biotinylated carbon nanohorns were solid-phased (5 mg/ml) and 100 μl of control suspension of magnetic beads wherein biotin was not solid-phased (5 mg/ml) were poured into a 1.8 ml plastic tube respectively, and washed twice with 200 μl of 2% bovine serum albumin, 50 mM TBS. Then solutions thus obtained were suspended in the same buffer and the suspensions were incubated for 20 minutes at room temperature, thereby a blocking operation with bovine serum albumin to inhibit binding of nonspecific phages was completed.

The undiluted solutions of the phage libraries were diluted, and phage solutions were prepared so that the phage titers in 200 μl of 2% bovine serum albumin, 0.1% Tween-20, 50 mM TBS were $2.7 \times 10^{11}$ pfu/ml for D12 library and $1.2 \times 10^{11}$ pfu/ml for C7C library. The phage titers were obtained according to an ordinary method (Phage Display—A Laboratory Manual, Cold Spring Harbor Laboratory Press, 2001).

In order to exclude unwanted background binding of peptide phages recognizing bead moieties in advance, the following prepanning operation was conducted. In other words, 200 μl of phage solution (phage titer of D12 library was $2.7 \times 10^{11}$ pfu/ml, and that of C7C library was $1.2 \times 10^{11}$ pfu/ml) was added to 0.5 mg of beads wherein carbon nanohorns were not solid-phased and to which blocking was conducted with bovine serum albumin, and the mixture was incubated for 4 hours at room temperature. Next, magnetic beads in the phage solution were adsorbed to a magnet, and the supernatant phage solution was poured into another tube. Further, bead solution was washed once with 50 μl of 2% bovine serum albumin, 0.1% Tween-20, 50 mM TBS, and total of 250 μl of prepanned phage solution, including the washing liquid, was obtained.

250 μl of prepanned phage library solution was added to beads wherein biotinylated carbon nanohorns were solid-phased (corresponding to about 70 μg of carbon nanohorns) and to which blocking was conducted with bovine serum albumin, and the mixture was incubated while being agitated slowly by a rotator (RT-50, Taitec, Tokyo) for 18 hours at room temperature. The magnetic beads were washed 10 times with 1 ml of 0.1% Tween-20, 50 mM TBS. After the last washing, 1 ml of elution buffer [2 M glycine-HCl (pH 2.2), 1 mg/ml bovine serum albumin] was added to magnet beads wherein carbon nanohorns were solid-phased, and the mixture thus obtained was incubated for 10 minutes to elute phages bound to carbon nanohorns. Beads wherein biotinylated carbon nanohorns were solid-phased were adsorbed with a magnet, and 1 ml of solution of the eluted phages collected from supernatant was poured into another tube. 150 μl of 1 M Tris-HCl (pH 9.1) was added to the collected phage solution to neutralize the eluted solution, and titer of eluted phages was measured.

The phage-eluted solution obtained by the above operation was infected with a bacterial strain ER2738 [F 'lacI$^q$ Δ(lacZ) M15 proA$^+$B$^+$ zzf::Tn10 (TetR) fhuA2 supE thi Δ(lac-proAB) Δ(hsdMS-mcrB) 5 ($r_k^-m_k^-$ McrBC$^-$)], which was logarithmically growing in 20 ml of LB, and incubated for 4.5 hours at 37° C. while being agitated vigorously with an incubator shaker (BR-40LF, Taitec). The incubated solution of the infected phage was poured into a centrifuge tube (50 ml, Beckman, California), and centrifuged twice at 4° C., 10000 rpm, for 10 minutes, with a Beckman centrifuge (Beckman, JA-12 rotor) to remove the strain ER2738, and supernatant phage solution was poured into another tube. 3.5 ml (⅙ amount) of 20% polyethylene glycol 6000 (hereinafter referred to as PEG 6000, Fluka, Buchs), 2.5 M NaCl solution were added to the phage solution, and the resultant mixture was agitated well with a mixer (S-100, Taitec) and incubated at 4° C. for 12 hours to precipitate the phage.

The precipitated phage was collected by conducting centrifugation at 4° C., 10000 rpm, for 10 minutes, with a Beckman centrifuge. The precipitated phage was further centrifuged at 4000 rpm for 1 minute to completely remove a small amount of supernatant remained therein. 1 ml of TBS was added to the obtained phage precipitate, and the mixture was cooled on ice, then the phage was suspended gently. This phage suspension was poured into a 1.8 ml plastic tube, and centrifuged at 15000 rpm for 5 minutes with a high-speed microcentrifuge (TMA-II rotor, Tomy Seiko Co., Ltd., Tokyo), then the supernatant was poured into another tube, and residues that did not suspend were removed. Again, 200 μl of 20% PEG 6000 and 2.5 M NaCl were added to the phage solution and the resultant mixture was agitated well with the mixer, and incubated for 1 hour on ice to precipitate the phage. Next, centrifugation was conducted with the high-speed microcentrifuge at 15000 rpm for 10 minutes to collect phage precipitate. 200 μl of 0.02% NaN$_3$ (Wako Pure Chemical Industries, Ltd., Osaka), and 50 mM TBS were added to the obtained phage precipitate and the phage precipitate was suspended completely. Residues that did not suspend were removed by centrifugation at 15000 rpm for 5 minutes with the high-speed microcentrifuge. The titer of the concentrated phage solution thus obtained was measured.

A series of the above-mentioned operations to phages, comprising binding to a target molecule (in this case, carbon nanohorns), washing, collecting, and proliferation with *E. coli*, is called a panning operation. By repeating the panning operation, a phage clone strongly and specifically binding to a target molecule can be concentrated. In this case, after the first panning operation, the second panning operation and the panning operations after that, comprising binding to beads wherein biotinylated carbon nanohorns were solid-phased, washing, collecting and proliferating, were repeatedly conducted with the use of phages which were once proliferated by using *E. coli*. Among the conditions of the second panning operation and the panning operations after that, the followings were different from those of the first panning operation. In brief, titer of phage added in the second panning operation and the panning operations after that was adjusted to $2.7 \times 10^{10}$ for D12 library and $1.2 \times 10^{10}$ for C7C library. The concentrations of Tween-20 in the solution for suspending the concentrated phage, reaction buffer and washing buffer of beads wherein biotinylated carbon nanohorns were solid-phased, were 0.3% at the second panning operation, and 0.5% at the third panning operation and the panning operations after that.

Figure 2:
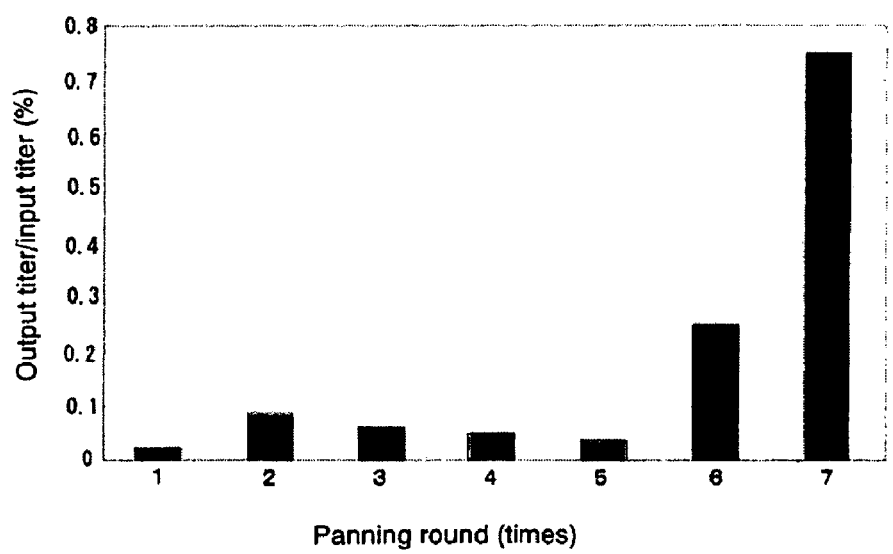
FIG. 2 is a graph showing the result of the panning experiment of C7C peptide display library to the solid-phased carbon nanohorns in Example 1 of the present invention. The ratio of output titer to input titer of each panning round is shown.

The changes in the ratio of input titer (titer of phage added to the target molecule) and output titer (titer of phage eluted from the target molecule after washing) in the panning experiment using D12 library are shown in FIG. 1, and the changes in the ratio of input titer and output titer in the panning experiment using C7C library are shown in FIG. 2.

Phages obtained in $5^{th}$ and $6^{th}$ rounds with D12 library and those obtained in $6^{th}$ and $7^{th}$ rounds with C7C library were cloned according to an ordinary method (Phage Display—A Laboratory Manual, Cold Spring Harbor Laboratory Press, 2001), respectively, and base sequences of the displayed peptide moieties were determined. The base sequence determination was conducted by dideoxy-terminator with the use of a primer corresponding to a complementary strand of the base sequence located at downstream by 96 bases from the displayed peptide region [−96gIII sequencing primer (5'-$^{HO}$1CCCTCATAGTTAGCGTAACG-3') (Seq. ID No. 32), NEB, Beverly] (CEQ DTCS Quick start kit, Beckman, California). For migration of reactant and data analysis, a capillary sequencer (CEQ2000, Beckman) was used.

Some of displayed peptide sequences expected from the determined base sequences are shown for D12 library in FIG. 3 (Seq. ID Nos. 1 and 3 to 7), and for C7C library in FIG. 4 (Seq. ID Nos. 2, 8 to 10 and 25). Among them, for a peptide sequence DYFSSPYYEQLF (Seq. ID No. 1), displayed by NHD12-5-2 phage obtained in the $5^{th}$ panning operation of D12 library, 15 out of 33 clones (45%) from the $5^{th}$ panning operation had the same sequence, while as to clones from the $6^{th}$ panning operation, 13 out of 15 (87%) had the same sequence. Similarly, for a peptide sequence YDPFHII (Seq. ID No. 2), displayed by NHC-6-2 phage obtained in the $6^{th}$ panning operation of C7C library, 7 out of 14 clones (50%) from the $6^{th}$ panning operation had the same sequence, while as to clones from the $7^{th}$ panning operation, 10 out of 14 (71%) had the same sequence. One of the reasons why a specific phage clone makes up a larger share of the population in proportion to the number of panning rounds is that the phage clone has strong ability to bind to the target molecule.

Phages displaying the peptides shown in FIG. 3 (Seq. ID Nos. 1 and 3 to 7), and in FIG. 4 (Seq. ID Nos. 2, 8 to 10 and 25) were cloned and ability to bind to carbon nanohorns and carbon nanotubes in cloned state was evaluated as shown in Example 4.

EXAMPLE 2

Single-wall carbon nanotube synthesized by chemical vapor deposition, Hipco (Carbon Nanotechnologies Inc., Texas), was treated with $1 \times 10^{-5}$ Torr for 5 hours at 1750° C., and then reflux was conducted for 30 minutes at about 130° C. in nitric acid at a concentration of about 70%. After that, neutralization with sodium hydroxide and washing with distilled water were conducted, and single-wall carbon nanotubes having a functional group (including a carboxyl group) were prepared.

The nitric acid-treated single-wall carbon nanotubes thus obtained were biotinylated and solid-phased on streptavidin-coated magnetic beads in a same manner as shown in Example 1. With the use of the solid-phased carbon nanotubes, panning experiment was conducted with D12 library and C7C library in a same manner as shown in Example 1, with the proviso that for C7C library, input titer of phage at the $1^{st}$ round was set at $2.4 \times 10^{11}$, and after that, it was set at $1.2 \times 10^{10}$ as in Example 1.

Figure 5:
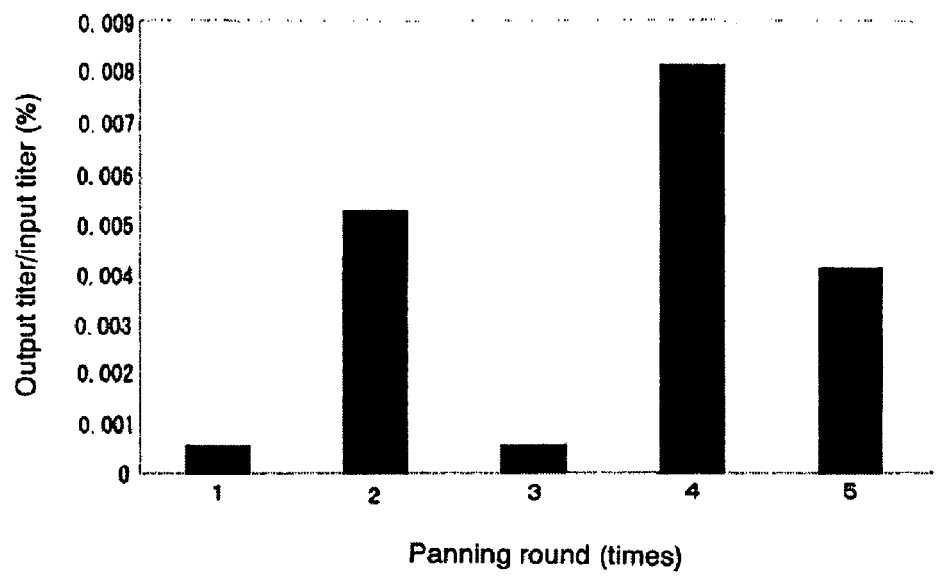
FIG. 5 is a graph showing the result of the panning experiment of D12 peptide display library to the solid-phased carbon nanotubes in Example 2 of the present invention. The ratio of output titer to input titer of each panning round is shown.
Figure 6:
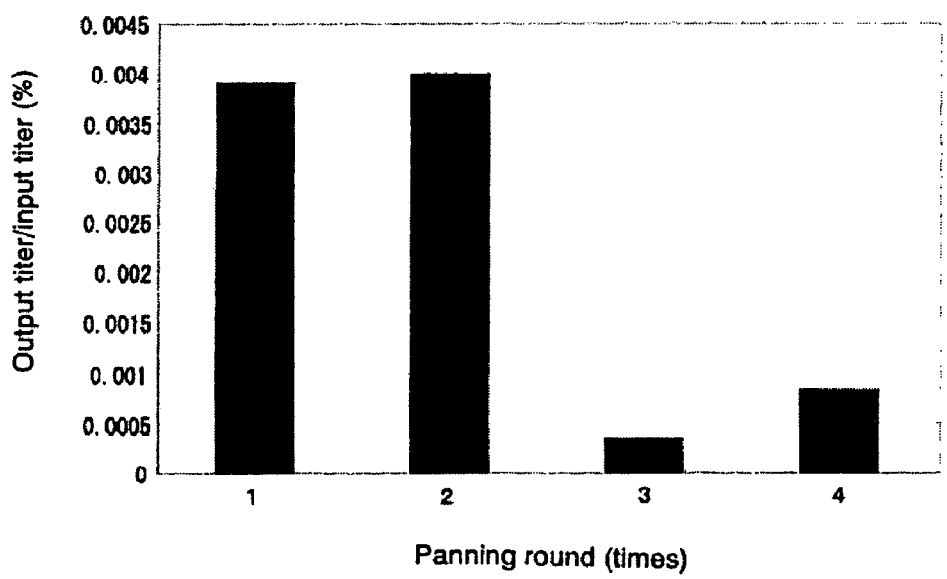
FIG. 6 is a graph showing the result of the panning experiment of C7C peptide display library to the solid-phased carbon nanotubes in Example 2 of the present invention. The ratio of output titer to input titer of each panning round is shown.

The changes in the ratio of input titer and output titer in the panning experiment using D12 library are shown in FIG. 5, and the changes in the ratio of input titer and output titer in the panning experiment using C7C library are shown in FIG. 6. Some of displayed peptide sequences expected from the determined base sequences are shown for D12 library in FIG. 7 (Seq. ID Nos. 11 to 15 and 26 to 28), and for C7C library in FIG. 8 (Seq. ID Nos. 29 to 30). The ability to bind to carbon nanohorns and carbon nanotubes in cloned state was evaluated as shown in Example 4.

EXAMPLE 3

Figures 9, 10:
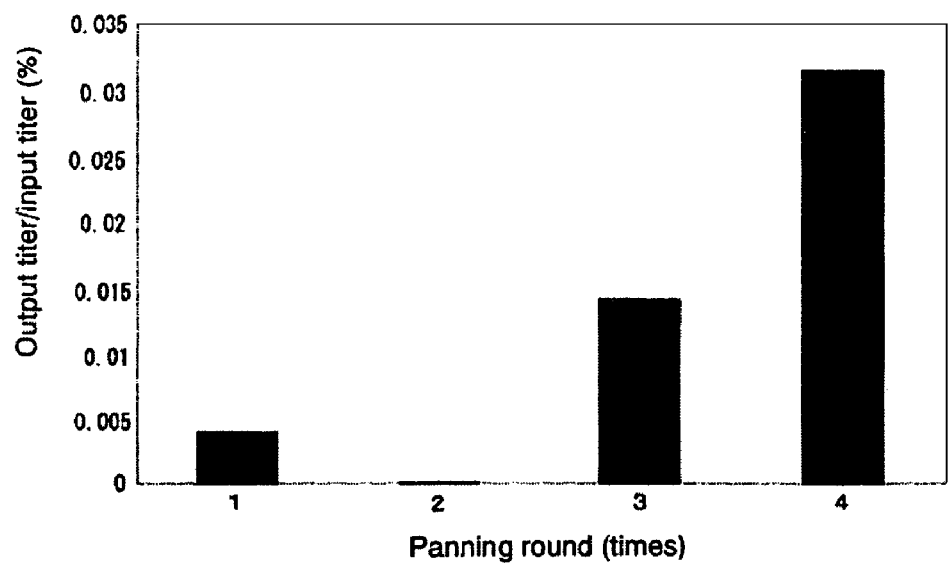
FIG. 9 is the result of the panning experiment of D12 peptide display library to the carbon nanotubes in Example 3 of the present invention. The ratio of output titer to input titer of each panning round is shown.
FIG. 10 is a chart showing clone names of phage clones obtained by the panning experiment of D12 peptide display library to the carbon nanotubes in Example 3 of the present invention, and peptide sequences displayed by the phages. Figure discloses SEQ ID NOS: 16-19, 31 and 20, respectively, in order of appearance.

With regard to a suspension of single-wall carbon nanotubes, unlike that of carbon nanohorns, it is possible to separate only carbon nanotubes by centrifugation. In the same manner as shown in Example 1, panning operations to untreated single-wall carbon nanotubes were conducted with the use of D12 library. However, prepanning operation was conducted with a 96-well ELISA plate (Immulon 4HBX, Dynex Technologies, Inc., VA), binding reaction of phages was set to 2 hours, and separation of single-wall carbon nanotubes after the reaction was conducted by putting the reaction liquid into a 1.8 ml plastic tube and centrifuging it for 8 minutes at 15000 rpm using the high-speed microcentrifuge (mentioned above). Further, input titer of phage was set at $2.7 \times 10^{11}$ in the $1^{st}$ to $2^{nd}$ rounds, and $2.7 \times 10^{10}$ in the rounds after that. The changes in the ratio of input titer and output titer are shown in FIG. 9. Some of displayed peptide sequences expected from the determined base sequences are shown in FIG. 10 (Seq. ID Nos. 16 to 20 and 31). Out of 19 phage clones whose sequences were determined, 7 clones had the same sequence as the peptide sequence displayed by a phage clone of Hip2 phages (Seq. ID No. 17). Similarly, 2 clones had the same sequence as the peptide sequence displayed by a phage clone of Hip1 phages (Seq. ID No. 16), and 2 clones had the same sequence as the peptide sequence displayed by a phage clone of Hip6 phages (Seq. ID No. 18). The ability to bind to carbon nanohorns and carbon nanotubes in cloned state was evaluated as shown in Example 4.

EXAMPLE 4

With the use of phage clones obtained in Examples 1, 2 and 3, the ability to bind to solid-phased carbon nanohorns and solid-phased single-wall carbon nanotubes were evaluated based on the following experiment. Nitric acid-treated carbon nanohorns and nitric acid-treated single-wall carbon nanotubes were solid-phased on streptavidin-coated magnetic beads in a same manner as shown in Examples 1 and 2. Solid-phased sample, 1/20 in the amount of previously used (corresponding to about 3.5 μg of carbon nanohorns), was added to a 96-well plate (Falcon assay plate, U-bottom, Becton Dickinson, New Jersey), and buffer was changed for 200 μl of 2% bovine serum albumin, TBS, with a magnetic particle concentrator (MPC-96, Dynal Biotech, Oslo), and incubation was conducted for 1 hour. Next, washing was conducted 3 times with 200 μl of 0.5% Tween-20, TBS, and a phage clone prepared in 200 μl of 2% bovine serum albumin, 0.5% Tween-20, 50 mM TBS so that the phage titer was adjusted to $5 \times 10^8$ pfu/ml was added, and the resultant mixture was incubated for 2 hours while being agitated at room temperature with a mild mixer (PR-12, Taitec).

Then the mixture was washed 10 times with 200 μl of 0.5% Tween-20, TBS, by using a magnetic particle concentrator. Next, the phage binding to solid-phased beads was quantified as follows: anti-M13 antibodies conjugated with horseradish peroxydase were bound to the phages with the use of an ELISA kit for detecting M13 phage (Detection Module Recombinant Phage Antibody System, Amersham Pharmacia Biotech, Little Chalfont Buckinghamshire); 2',2'-azino-bis (3-ethylbenzthiazoline-6-sulphonic acid)diammonium salt (ABTS), which is a coloring substrate, was added to the antibodies together with hydrogen peroxide; the absorbance ($A_{415\,nm}$) was measured. For the control phage clones, clones displaying N1 which does not have random peptides, and clones displaying N2 (Seq. ID No. 22), N3 (Seq. ID No. 23), N4 (Seq. ID No. 24) peptides obtained from an undiluted solution of D12 library wherein panning operation was not conducted, were used.

Figure 11:
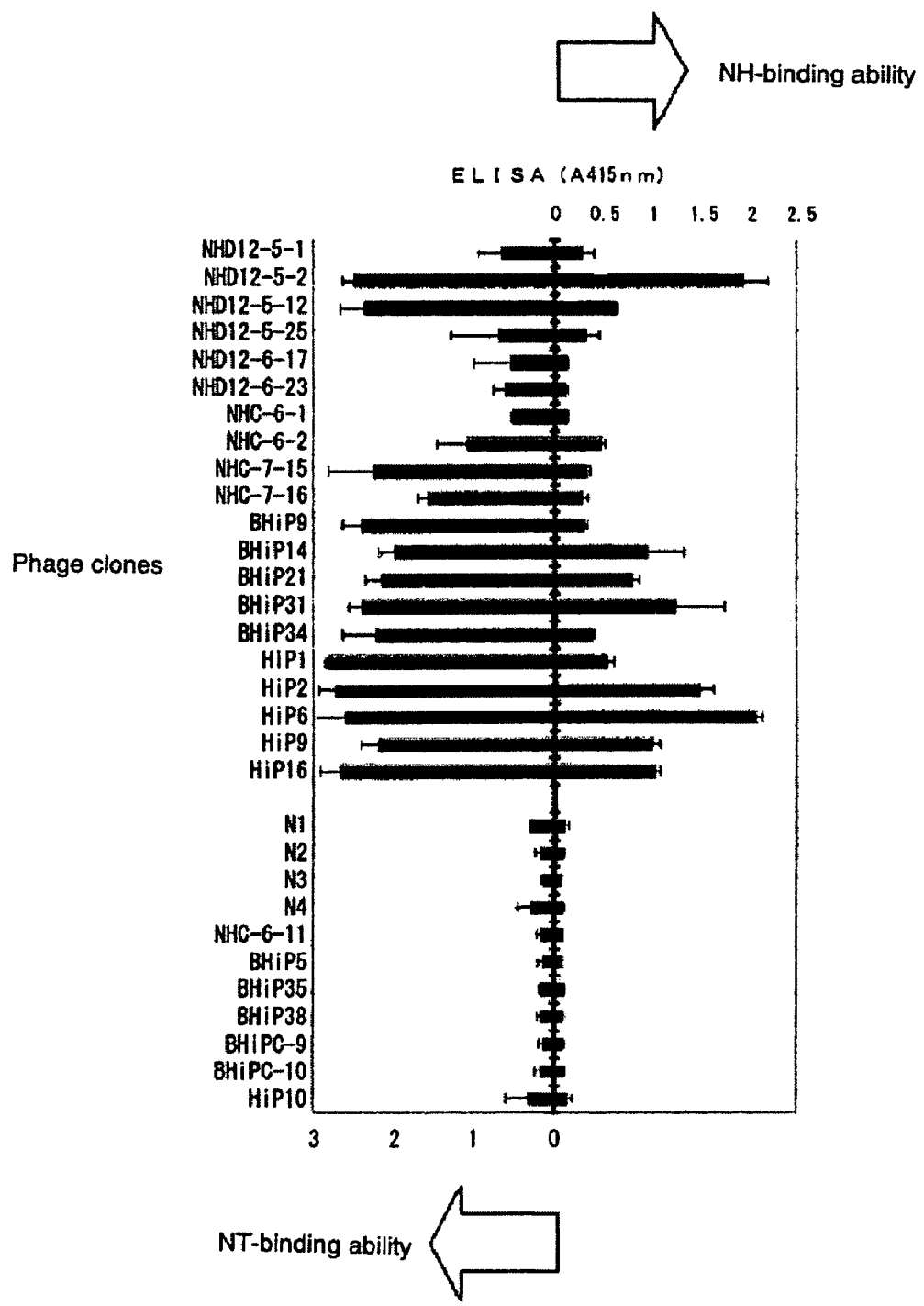
FIG. 11 is a graph showing the result of the experiment of binding ability to the solid-phased carbon nanohorns, the solid-phased single-wall carbon nanotubes in Example 4 of the present invention. The binding ability of phage clones to each sample was evaluated by ELISA twice, and the variation was figured out. The binding ability to the solid-phased carbon nanohorns (NH) and to the solid-phased carbon nanotubes (NT) are shown as absorbance of ELISA at the top and the bottom of the graph, respectively. According to the classification based on the difference in binding ability of phage clones, two groups (right population and left population) are shown.

The results are summarized in FIG. 11. 20 out of 27 clones exhibited strong binding to either of the samples, nitric acid-treated carbon nanohorns or nitric acid-treated single-wall carbon nanotubes. Every clone showed its own characteristics as to the degree of their ability to bind to carbon nanohorns and carbon nanotubes evaluated with ELISA. In other words, it has been revealed that NHD12-5-2 phage obtained in the election to nitric acid-treated carbon nanohorns which displays a peptide shown by Seq. ID No. 1 strongly binds to both carbon nanohorns and carbon nanotubes, while BHiP9 phage obtained in the election to nitric acid-treated single-wall carbon nanotubes which displays a peptide shown by Seq. ID No. 11 binds to carbon nanotubes more strongly than to carbon nanohorns. As the peptide sequence displayed by the phage having the latter characteristics is used, use in the field of nanobiotechnology of peptides and artificial proteins wherein delicate structural changes in nanographite structures are differentiated is considered.

As 7 out of 27 clones only showed the same level of binding as control to any of the samples, it is considered that peptides displayed by these 7 clones (Seq. ID Nos. 25 to 31) have no affinity with nanographite structures.

Figure 12:
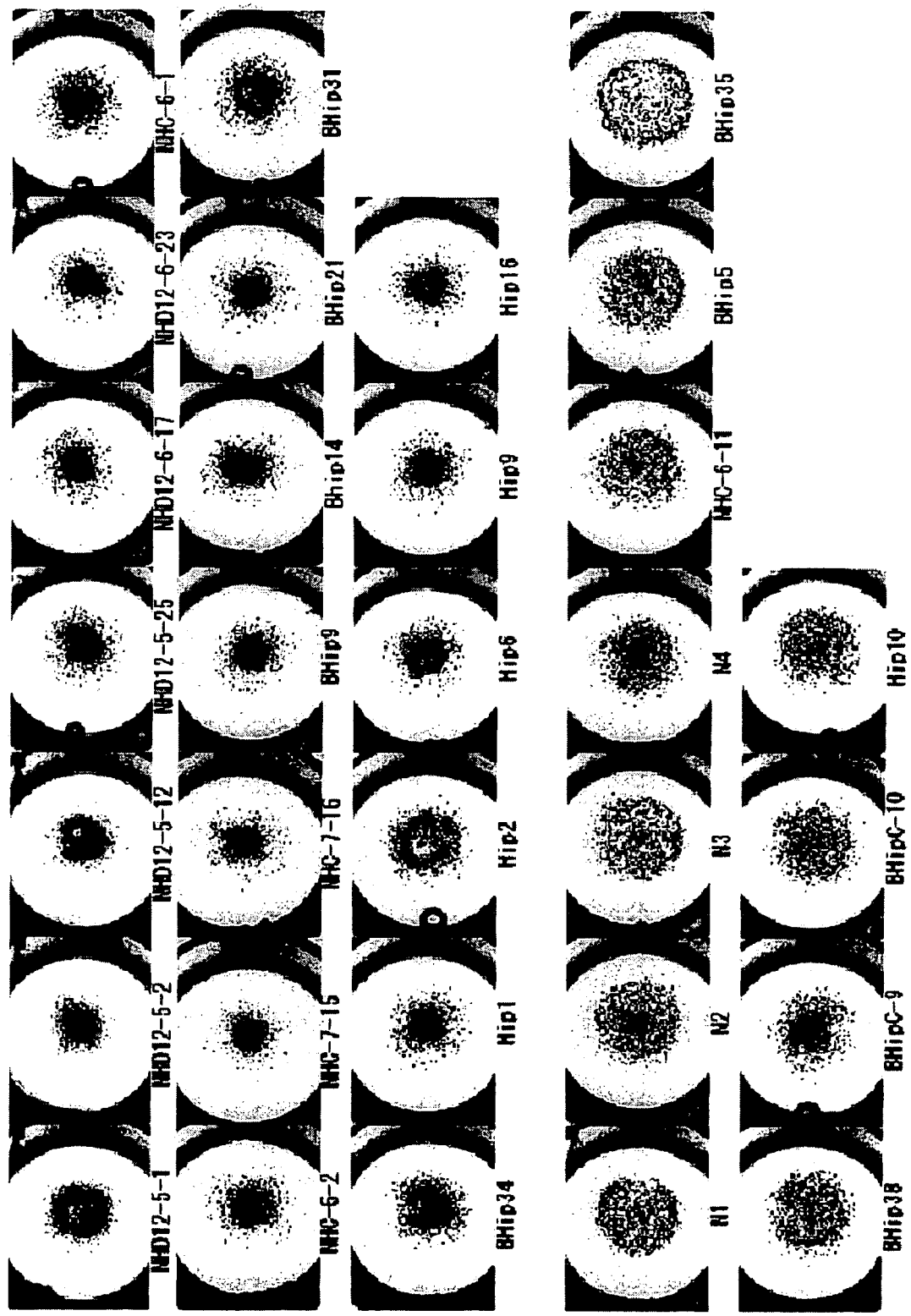
FIG. 12 is a set of photographs showing the result of the agglutination test of oxygen-treated carbon nanohorns with phage clones in Example 4 of the present invention. The cloned phages were added to the suspension of oxygen-treated carbon nanohorns at the titer $5 \times 10^8$, and the mixture was incubated for 2.5 hours at room temperature, then the precipitate was observed with a stereo light microscope.

It has been shown that many of the obtained phage peptides bind to nanographite structures solid-phased on magnetic beads. Next, ability of phages to bind to carbon nanohorns not solid-phased on magnetic beads was evaluated by a phage agglutination test. Firstly, single-wall carbon nanohorns were heat-treated at 420° C. for 10 minutes in oxygen atmosphere of 760 Torr to prepare single-wall carbon nanohorns having a functional group (including a carbonyl group). The oxygen-treated carbon nanohorns were suspended in 0.5% Tween-20, TBS solution, and the suspension was added to a 96-well plate (cell-culture-treated 96 microplate/Round bottom, IWAKI) by 200 μl each, and to this suspension, cloned phages were added at a titer $5 \times 10^8$. The mixture was incubated for 2.5 hours at room temperature, and then photographs of the precipitate were taken through a stereo light microscope (WILD M10, Leica, Switzerland). The results are shown in FIG. 12. In regard to 20 clones, precipitates of agglutinated carbon nanohorns were clearly observed near the center of the plates. It is considered that this is due to the occurrence of a phenomenon similar to the agglutination reaction of erythrocytes caused by antibodies against erythrocytes, and that it indicates the ability of phages to bind to carbon nanohorns. These 20 clones were in complete correspondence with 20 clones where strong binding to at least either of the samples, nitric acid-treated carbon nanohorns or nitric acid-treated single-wall carbon nanotubes was observed in the ELISA experiment. This result strongly excludes the possibility that phages displaying peptides do not recognize nanographite structures but recognize a molecule, which is not the original target, such as biotin, streptavidin, magnetic beads, etc., in the ELISA experiment.

Further, in order to indicate that displayed peptide moieties play an important role in the observed binding of phage clones to carbon nanohorns, and that the binding is specific to peptide sequences, the following peptide competitive test was conducted with the use of NHD12-5-2 phage displaying the peptide shown by Seq. ID No. 1.

1 μg/35 μl of streptavidin solution (NEB) was prepared with TBS, and added to a 96-well ELISA plate (Immulon 4HBX, Dynex Technologies, VA) by 35 μl each, and incubated in an airtight container for 1 hour at 37° C. to solid phase streptavidin on the ELISA plate. Then, nonadsorbed streptavidin solution was discarded, and the plate was washed with 200 μl of TBS chilled to 4° C. Subsequently, 200 μl of 2% bovine serum albumin, TBS solution was added and the resultant mixture was incubated for 1 hour. The mixture was washed 3 times with 200 μl of 0.5% Tween-20, TBS, and 100 μl of MES suspension of biotinylated carbon nanohorns was added, and incubation was conducted for 1 hour while agitating with a mild mixer (PR-12, Taitec) at room temperature. Next, 10 μl of 1 mM d-biotin, 2% bovine serum albumin, TBS were added, and the resultant mixture was incubated for 5 minutes, and unreacted streptavidin sites were saturated with biotin. Washing was conducted 3 times with 200 μl of 0.5% Tween-20, TBS.

Figure 13:
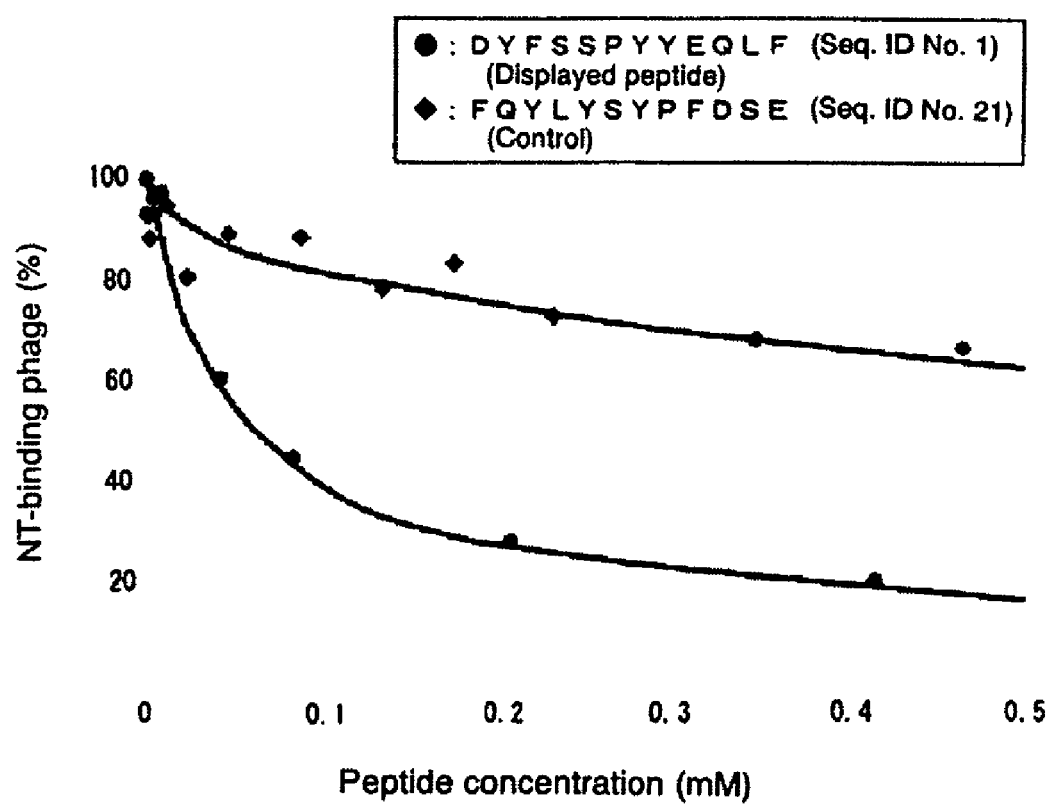
FIG. 13 is a graph showing the result of the binding-competitive test using the NHD12-5-2 clone and the synthetic peptide in Example 4. The binding of the NHD12-5-2 phage displaying a peptide shown by Seq. ID No. 1 to the solid-phased carbon nanohorns in the presence of a synthetic peptide at the indicated concentration was evaluated by ELISA, and shown in comparison to the binding in the absence of a peptide, which was set at 100%. As a peptide to be coexistent with, a synthetic peptide having Seq. ID No. 1 and a control peptide (Seq. ID No. 21) having the same amino acid composition as Seq. ID No. 1, but different in its sequence, were used.

Various amounts of the peptide DYFSSPYYEQLF (Seq. ID No. 1), or the peptide FQYLYSYPFDSE (Seq. ID No. 21) (purity 95% or more, based on HPLC grade, Anygen, Kwang ju), were added to 200 μl of 0.8% dimethyl sulphoxide (hereinafter referred to as DMSO), 2% bovine serum albumin, 0.5% Tween-20, TBS, and moreover, NHD12-5-2 clone was added at titer $1.8 \times 10^8$. The mixture thus obtained was added to the 96-well plate wherein biotinylated carbon nanohorns were solid-phased, and incubation was conducted for 18 hours while agitating with a mild mixer (PR-12, Taitec) at room temperature. Then washing was conducted 10 times with 200 μl of 0.5% Tween-20, TBS. After the last washing, bound phages were quantified by ELISA to examine binding ability of phages in the presence of peptide at each concentration. The value of ELISA obtained for NHD12-5-2 clone to which peptide was not added was set at 100%, and inhibitory effect caused by the addition of peptides on binding ability was examined and the results are shown in FIG. 13. Binding of NHD12-5-2 clone to solid-phased carbon nanohorns was inhibited in proportion to the increase in the concentration of the added synthetic peptide, DYFSSPYYEQLF (Seq. ID No. 1). However, inhibitory effect caused by the addition of the synthetic peptide having the same amino acid composition but different in its sequence, FQYLYSYPFDSE (Seq. ID No.

21), was not observed significantly. This result indicates that peptide moieties displayed by phages play an important role in the binding of NHD12-5-2 clones to solid-phased carbon nanohorns, and that the binding is specific to peptide sequences.

The summary of the above-mentioned binding evaluation experiment is shown in FIG. 14. It has been revealed that sequences of aromatic amino acids such as tryptophan, tyrosine, phenylalanine, appear frequently in all clones showing strong binding ability. Further, there is a characteristic that histidine frequently appears in the clones showing strong binding ability.

INDUSTRIAL APPLICABILITY

With the use of the peptide sequences specifically recognizing nanographite structures of the present invention, it becomes possible to easily construct a complex of a nanographite structure and a peptide, a complex of a nanographite structure and other molecule mediated by a peptide, a complex of a nanographite structure and an artificial protein generated based on a peptide sequence, etc. These complexes can be applied in the field of nanobiotechnology, such as alteration of property or alignment on nanometer-scale of nanographite structures.

The invention claimed is:

1. A peptide capable of binding to a carbon nanohorn or a carbon nanotube, which comprises the amino acid sequence of Seq. ID No. 1.

2. A phage capable of binding to a carbon nanohorn or a carbon nanotube, wherein the phage displays a peptide comprising the amino acid sequence of Seq. ID No. 1 on its particle surface.

3. An artificial protein capable of binding to a carbon nanohorn or a carbon nanotube, wherein the artificial protein comprises a peptide comprising the amino acid sequence of Seq. ID No. 1.

4. A chimeric molecule capable of binding to a carbon nanohorn or a carbon nanotube, wherein the chimeric molecule comprises the amino acid sequence of Seq. ID No. 1.

5. A nanographite structure complex comprising:
(a) a peptide comprising the amino acid of Seq. ID No 1,
(b) the artificial protein capable of binding to a carbon nanohorn or a carbon nanotube, wherein the artificial protein comprises a peptide comprising the amino acid sequence of Seq. ID No. 1, or
(c) the chimeric molecule capable of binding to a carbon nanohorn or a carbon nanotube, wherein the chimeric molecule comprises the amino acid sequence of Seq. ID No. 1,
wherein the peptide, the artificial protein or the chimeric protein is bound to a carbon nanohorn or a carbon nanotube.

* * * * *